(12) United States Patent
Ferree et al.

(10) Patent No.: US 8,167,915 B2
(45) Date of Patent: May 1, 2012

(54) METHODS AND APPARATUS FOR TREATING SPINAL STENOSIS

(75) Inventors: Bret A. Ferree, Cincinnati, OH (US); Rich Mueller, San Diego, CA (US); Forrest Samuel, San Diego, CA (US); Andrew Schafer, San Diego, CA (US); Benjamin Arnold, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 1083 days.

(21) Appl. No.: 11/540,318

(22) Filed: Sep. 28, 2006

(65) Prior Publication Data
US 2007/0093825 A1 Apr. 26, 2007

Related U.S. Application Data

(60) Provisional application No. 60/722,065, filed on Sep. 28, 2005.

(51) Int. Cl.
*A61B 17/88* (2006.01)
*A61B 17/70* (2006.01)

(52) U.S. Cl. ......... 606/279; 606/246; 606/248; 606/249

(58) Field of Classification Search .................. 606/248, 606/249, 276
See application file for complete search history.

(56) References Cited

U.S. PATENT DOCUMENTS

| | | |
|---|---|---|
| 2,677,369 A | 5/1954 | Knowles |
| 3,426,364 A | 2/1969 | Lumb |
| 3,648,691 A | 3/1972 | Lumb |
| 3,875,595 A | 4/1975 | Froning |
| 4,369,769 A | 1/1983 | Edwards |
| 4,554,914 A | 11/1985 | Kapp |
| 4,570,618 A | 2/1986 | Wu |
| 4,599,086 A | 7/1986 | Doty |
| 4,604,995 A | 8/1986 | Stephens |
| 4,611,582 A | 9/1986 | Duff |
| 4,643,178 A | 2/1987 | Nastari |
| 4,685,447 A | 8/1987 | Iversen |
| 4,696,290 A | 9/1987 | Steffee |
| 4,728,329 A | 3/1988 | Mansat |
| 4,795,466 A | 1/1989 | Stuhmer |
| 4,805,602 A | 2/1989 | Puno |
| 4,913,134 A | 4/1990 | Luque |
| 4,917,700 A | 4/1990 | Aikins |
| 4,946,378 A | 8/1990 | Hirayama |
| 4,969,888 A | 11/1990 | Scholten |
| 5,011,484 A | 4/1991 | Breard |
| 5,030,220 A | 7/1991 | Howland |
| 5,035,716 A | 7/1991 | Downey |
| 5,047,055 A | 9/1991 | Bao |
| 5,059,194 A | 10/1991 | Michelson |
| 5,084,049 A | 1/1992 | Asher |
| 5,092,866 A | 3/1992 | Breard |
| 5,092,893 A | 3/1992 | Smith |
| 5,123,926 A | 6/1992 | Pisharodi |

(Continued)

*Primary Examiner* — Thomas J Sweet
*Assistant Examiner* — Ellen C. Hammond
(74) *Attorney, Agent, or Firm* — NuVasive, Inc.; Jonathan Spangler; Jennifer Russell

(57) ABSTRACT

This invention relates generally to spine surgery and, in particular, to methods and apparatus for treating spinal stenosis. The methods comprising gaining access to an interspinous space, abrading a portion of the superior spinous process, inserting an implant into the interspinous process space, verifying the position of the implant by observing the position of three radio-opaque markers embedded in the implant, and coupling the implant to the superior spinous process.

22 Claims, 16 Drawing Sheets

U.S. PATENT DOCUMENTS

| | | | |
|---|---|---|---|
| 5,167,662 A | 12/1992 | Hayes | |
| 5,180,381 A | 1/1993 | Aust et al. | |
| 5,180,393 A | 1/1993 | Commarmond | |
| 5,192,327 A | 3/1993 | Brantigan | |
| 5,282,863 A | 2/1994 | Burton | |
| 5,290,312 A | 3/1994 | Kojimoto | |
| 5,304,178 A | 4/1994 | Stahurski | |
| 5,306,309 A | 4/1994 | Wagner | |
| 5,352,225 A | 10/1994 | Yuan | |
| 5,375,823 A | 12/1994 | Navas | |
| 5,387,213 A | 2/1995 | Breard | |
| 5,390,683 A | 2/1995 | Pisharodi | |
| 5,395,372 A | 3/1995 | Holt | |
| 5,415,661 A | 5/1995 | Holmes | |
| 5,443,514 A | 8/1995 | Steffee | |
| 5,458,638 A | 10/1995 | Kuslich | |
| 5,458,641 A | 10/1995 | Ramirez | |
| 5,458,643 A | 10/1995 | Oka | |
| 5,470,333 A | 11/1995 | Ray | |
| 5,480,401 A | 1/1996 | Navas | |
| 5,496,318 A | 3/1996 | Howland | |
| 5,505,732 A | 4/1996 | Michelson | |
| 5,514,180 A | 5/1996 | Heggeness | |
| 5,534,028 A | 7/1996 | Bao | |
| 5,534,029 A | 7/1996 | Shima | |
| 5,540,688 A | 7/1996 | Navas | |
| 5,540,689 A | 7/1996 | Sanders | |
| 5,549,679 A | 8/1996 | Kuslich | |
| 5,562,736 A | 10/1996 | Ray | |
| 5,593,409 A | 1/1997 | Michelson | |
| 5,609,634 A | 3/1997 | Voydeville | |
| 5,645,597 A | 7/1997 | Krapiva | |
| 5,645,599 A | 7/1997 | Samani | |
| 5,653,761 A | 8/1997 | Pisharodi | |
| 5,658,286 A | 8/1997 | Save | |
| 5,672,175 A | 9/1997 | Martin | |
| 5,674,295 A | 10/1997 | Ray | |
| 5,674,296 A | 10/1997 | Bryan | |
| 5,676,702 A | 10/1997 | Ratron | |
| 5,702,455 A | 12/1997 | Saggar | |
| 5,725,582 A | 3/1998 | Bevan | |
| 5,766,252 A | 6/1998 | Henry | |
| 5,814,046 A | 9/1998 | Hopf | |
| 5,824,098 A | 10/1998 | Stein | |
| 5,836,948 A * | 11/1998 | Zucherman et al. | 606/249 |
| 5,860,977 A | 1/1999 | Zucherman | |
| 5,865,846 A | 2/1999 | Bryan | |
| 5,876,404 A | 3/1999 | Zucherman | |
| 5,885,299 A | 3/1999 | Winslow | |
| 5,888,224 A | 3/1999 | Beckers | |
| 5,888,226 A | 3/1999 | Rogozinski | |
| 5,904,686 A | 5/1999 | Zucherman | |
| 5,976,186 A | 11/1999 | Bao | |
| 6,001,130 A | 12/1999 | Bryan | |
| 6,022,376 A | 2/2000 | Assell | |
| 6,048,342 A | 4/2000 | Zucherman | |
| 6,068,630 A | 5/2000 | Zucherman | |
| 6,074,390 A | 6/2000 | Zucherman | |
| 6,090,112 A | 7/2000 | Zucherman | |
| 6,113,639 A | 9/2000 | Ray | |
| 6,149,652 A | 11/2000 | Zucherman | |
| 6,156,038 A | 12/2000 | Zucherman | |
| 6,156,067 A | 12/2000 | Bryan | |
| 6,183,471 B1 | 2/2001 | Zucherman | |
| 6,190,387 B1 | 2/2001 | Zucherman | |
| 6,234,705 B1 | 5/2001 | Troxell | |
| 6,235,030 B1 | 5/2001 | Zucherman | |
| 6,238,397 B1 | 5/2001 | Zucherman | |
| 6,280,444 B1 | 8/2001 | Zucherman | |
| 6,290,700 B1 | 9/2001 | Schmotzer | |
| 6,332,882 B1 | 12/2001 | Zucherman | |
| 6,332,883 B1 | 12/2001 | Zucherman | |
| 6,355,038 B1 | 3/2002 | Pisharodi | |
| 6,379,355 B1 | 4/2002 | Zucherman | |
| 6,402,750 B1 | 6/2002 | Atkinson | |
| 6,419,676 B1 | 7/2002 | Zucherman | |
| 6,419,677 B2 | 7/2002 | Zucherman | |
| 6,451,019 B1 | 9/2002 | Zucherman | |
| 6,451,020 B1 | 9/2002 | Zucherman | |
| 6,478,796 B2 | 11/2002 | Zucherman | |
| 6,500,178 B2 | 12/2002 | Zucherman | |
| 6,514,255 B1 | 2/2003 | Ferree | |
| 6,514,256 B2 | 2/2003 | Zucherman | |
| 6,558,387 B2 | 5/2003 | Errico | |
| 6,626,944 B1 | 9/2003 | Taylor | |
| 6,652,527 B2 | 11/2003 | Zucherman | |
| 6,652,534 B2 | 11/2003 | Zucherman | |
| 6,669,697 B1 | 12/2003 | Pisharodi | |
| 6,695,842 B2 | 2/2004 | Zucherman | |
| 6,695,882 B2 | 2/2004 | Bianchi | |
| 6,699,246 B2 | 3/2004 | Zucherman | |
| 6,699,247 B2 | 3/2004 | Zucherman | |
| 6,712,819 B2 | 3/2004 | Zucherman | |
| 6,723,097 B2 * | 4/2004 | Fraser et al. | 606/86 A |
| 6,740,090 B1 | 5/2004 | Cragg | |
| 6,761,720 B1 | 7/2004 | Senegas | |
| 6,796,983 B1 | 9/2004 | Zucherman | |
| 7,172,593 B2 | 2/2007 | Trieu | |
| 7,201,775 B2 | 4/2007 | Gorensek | |
| 7,273,498 B2 | 9/2007 | Bianchi | |
| 2001/0020188 A1 | 9/2001 | Sander | |
| 2001/0021850 A1 | 9/2001 | Zucherman | |
| 2003/0040746 A1 | 2/2003 | Mitchell | |
| 2003/0045935 A1 | 3/2003 | Angelucci | |
| 2003/0060823 A1 | 3/2003 | Bryan | |
| 2004/0019356 A1 * | 1/2004 | Fraser et al. | 606/102 |
| 2004/0106995 A1 | 6/2004 | Le Couedic | |
| 2005/0165398 A1 | 7/2005 | Reiley | |
| 2006/0085070 A1 | 4/2006 | Kim | |
| 2006/0106381 A1 * | 5/2006 | Ferree et al. | 606/61 |
| 2006/0235532 A1 * | 10/2006 | Meunier et al. | 623/17.16 |
| 2006/0241601 A1 | 10/2006 | Trautwein | |
| 2006/0247634 A1 * | 11/2006 | Warner et al. | 606/61 |
| 2006/0293662 A1 * | 12/2006 | Boyer et al. | 606/61 |
| 2007/0032790 A1 * | 2/2007 | Aschmann et al. | 606/61 |
| 2007/0043361 A1 * | 2/2007 | Malandain et al. | 606/61 |
| 2007/0073292 A1 | 3/2007 | Kohm | |
| 2008/0015701 A1 | 1/2008 | Garcia | |
| 2008/0027438 A1 * | 1/2008 | Abdou | 606/61 |
| 2008/0319549 A1 | 12/2008 | Greenhalgh | |

* cited by examiner

METHODS AND APPARATUS FOR TREATING SPINAL STENOSIS

CROSS-REFERENCE TO RELATED APPLICATION

This application claims the benefit of the filing date under 35 U.S.C. 119(e) of provisional application entitled "Methods and Apparatus for Treating Spinal Stenosis," Ser. No. 60/722,065, filed Sep. 28, 2005, the entire contents of which is fully incorporated herein by reference.

BACKGROUND OF THE INVENTION

I. Field of the Invention

This invention relates generally to spine surgery and, in particular, to methods and apparatus for treating spinal stenosis.

II. Discussion of the Prior Art

Spinal stenosis is a narrowing of spaces in the spine which results in pressure on the spinal cord and/or nerve roots. This disorder usually involves the narrowing of one or more of the following: (1) the canal in the center of the vertebral column through which the spinal cord and nerve roots run, (2) the canals at the base or roots of nerves branching out from the spinal cord, or (3) the openings between vertebrae through which nerves leave the spine and go to other parts of the body. Pressure on the spinal cord and/or exiting nerve roots may give rise to pain or numbness in the legs and/or arms depending on the location within the spine (e.g. cervical, thoracic, lumbar regions). While spinal stenosis generally afflicts those of advanced age, younger patients may suffer as well.

A variety of treatments have been undertaken to alleviate or minimize the effects of spinal stenosis. One such technique is a laminectomy, which involves removing the lamina portion from the pathologic region. By removing the lamina, this procedure enlarges the spinal canal and thus relieves the pressure on the spinal chord and/or compressed nerves. While generally effective, some consider lamimectomy disadvantageous in that, as with any procedure involving bone removal, the resulting region of the spine may be further compromised from a mechanical standpoint. Moreover, elderly patients frequently have co-morbidities that increase the likelihood of complications, such as increased back pain, infection, and prolonged recovery.

Still other efforts at treating spinal stenosis involve placing spacer devices within the inter-spinous space to indirectly decompress the stenotic condition. These systems are characterized by being secured at the superior and inferior spinous processes. Having both ends of the spacer device coupled to the respective spinous processes disadvantageously limits both flexion and extension of the spine at that location, when it is believed that limiting extension is the key to relieving spinal stenosis. Moreover, the prior art inter-spinous spacers are typically constructed from materials (e.g. metal) with properties substantially different than that of the spinous processes themselves, which raises questions of whether the spinous processes will remodel around the spacer and thereby lose their ability to distract and thereby alleviate spinal stenosis.

The present invention is directed at overcoming, or at least improving upon, the disadvantages of the prior art.

SUMMARY OF THE INVENTION

The present invention is directed at treating spinal stenosis involving an inter-spinous spacer dimensioned to distract a stenotic inter-spinous space and further characterized as being affixed to only one of the two adjacent spinous processes to prevent spinal extension and allow spinal flexion. The inter-spinous spacer of the present invention may be used in the cervical, thoracic and/or lumbar spine. Although shown and described throughout this disclosure with the inter-spinous spacer affixed to the superior spinous process, it will be appreciated that the inter-spinous spacer of the present invention may also be affixed to the inferior spinous process without departing from the scope of the invention. Various mechanisms may be used to affix the inter-spinous spacer of the present invention to the given spinous process, including but not limited to one or more tethers (e.g. wire, cable, suture, allograft tissue, or other single or multi-filament members), one or more screws and/or any of a variety of clamping mechanisms.

According to an important aspect of the present invention, the inter-spinous spacer of the present invention is designed to fuse to the spinous process to which it is affixed over time, resulting in what is called "hemi-fusion" in that the spacer will be fused to only one spinous process. This is facilitated by abrading the surface of the spinous process (to preferably cause bleeding) where it will mate with the inter-spinous spacer of the present invention. This junction will fuse over time based, in part, on the fusion-enabling design and/or material of the inter-spinous spacer of the present invention. More specifically, the inter-spinous spacer of the present invention may be constructed from bone (e.g. allograft) material, which is readily known to enable fusion upon implantation. The inter-spinous spacer may also be constructed from non-bone materials (e.g. polyaryletheretherketone (PEEK) and/or polaryletherketoneketone (PEKK)) which are physically designed to promote fusion. This is accomplished, by way of example, by providing an interior lumen within the inter-spinous spacer which is dimensioned to receive fusion-inducing materials and which is in communication with the abraded surface of the given spinous process. Such fusion-promoting materials may include, but are not necessarily limited to BMP, demineralized bone matrix, allograft cancellous bone, autograft bone, hydroxy appetite, coral and/or other highly porous substances.

The present invention overcomes the drawbacks of the prior art by treating spinal stenosis while allowing spinal flexion with an implant constructed from materials with properties substantially closer to the properties of the spinous processes themselves than prior art devices. This advantageously minimizes the risk of the spinous processes remodeling around the inter-spinous spacer of the present invention, which advantageously prevents and/or minimizes the risk of a loss of distraction that may otherwise occur.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The spinal alignment system disclosed herein boasts a variety of inventive features and components that warrant patent protection, both individually and in combination.

Figure 1:
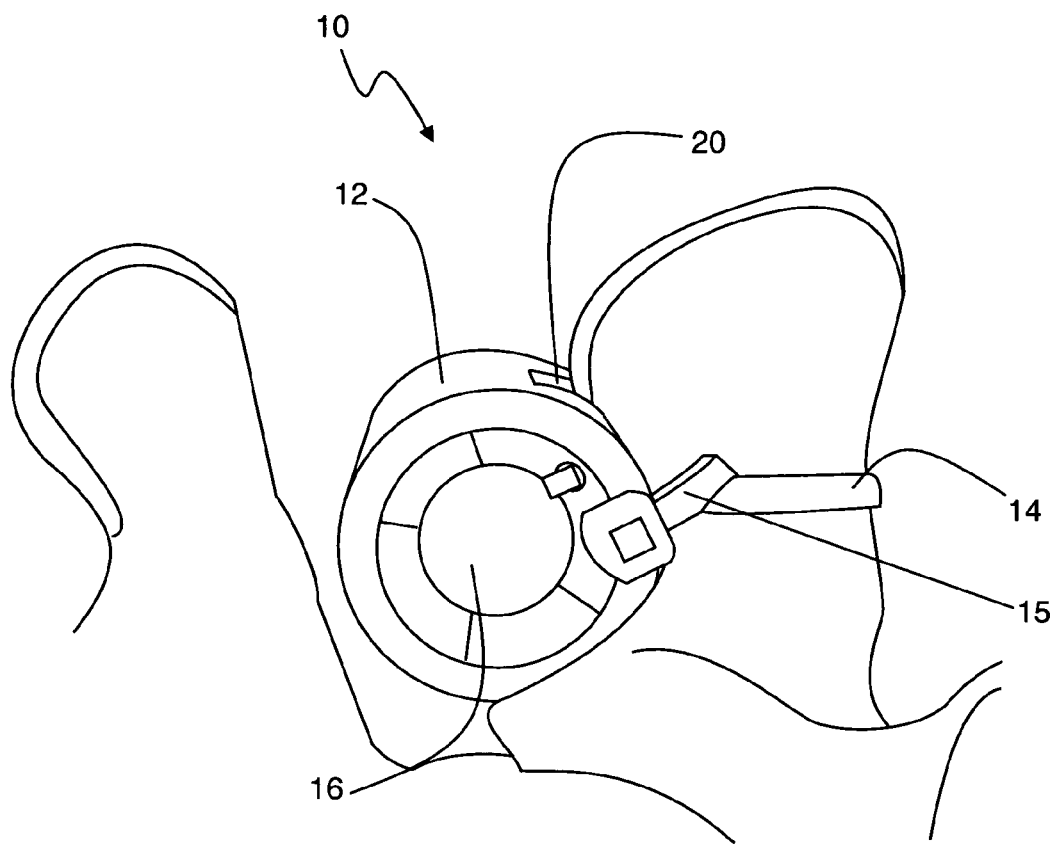
FIG. 1 is a perspective view of an inter-spinous spacer according to a first embodiment of the present invention in use affixed to a superior spinous process of a human spine.

FIG. 1 illustrates a perspective view of a spinous process spacer 10 of the present invention in use between two spinous processes in a human spine. The spacer assembly 10 includes a spacer 12, a primary spinous process tether 14, and two side tethers 15 (only one of which is shown in FIG. 1). The spacer 12, as illustrated in FIGS. 2-6, is generally cylindrical and includes a main chamber 16, a pair of insertion tool apertures 18, a fusion notch 20, and a pair of tether lumens 22. As will be described in greater detail below, the spacer 12 is (according to a preferred embodiment) coupled to only the superior spinous process such that the spacer 12, with no coupling to the inferior spinous process. This is accomplished, but way of example only, by securing the primary spinous process tether 14 to the superior spinous process (as a first step of affixation), followed by passing one side tether 15 through each of the tether lumens 22, in between the superior spinous process and the primary spinous process tether 14, and finally tightening each side tether 15 until the spacer 12 is generally transverse to the longitudinal axis of the spine.

The spacer 12 may be of bone or non-bone construction. The bone embodiment involves manufacturing the spacer 12 from a suitable allograft, including but not limited to clavicle, rib, humerus, radius, ulna, metacarpal, phalanx, femur, tibia, fibula, or metatarsal bone. The non-bone embodiment involves manufacturing the spacer 12 from suitable non-bone materials, including but not limited to polyaryletherketone (PEEK) and polyaryletherketoneketone (PEKK). In either event, the spacer 12 is designed to fuse to the superior spinous process over time, resulting in what is called "hemi-fusion" in that the spacer 12 will be fused to only one spinous process. This may be augmented by disposing any number of suitable fusion-inducing materials within the spacer 12, including but not limited to BMP1, 2, 3, 4, 5, 6, 7, 8, 9, 10, 11, 12, 13, 14 . . . n, demineralized bone matrix, allograft cancellous bone, autograft bone, hydroxy appetite, coral and/or other highly porous substance.

Although shown and described with regard to the superior spinous process, it will be appreciated that the spacer 12 may also be coupled to only the inferior spinous process without departing from the scope of the present invention. The spacer 12, once positioned, serves to distract the inter spinous process space, which advantageously restores foraminal height in stenotic patients and may also indirectly decompress the intervertebral space.

Figure 2:
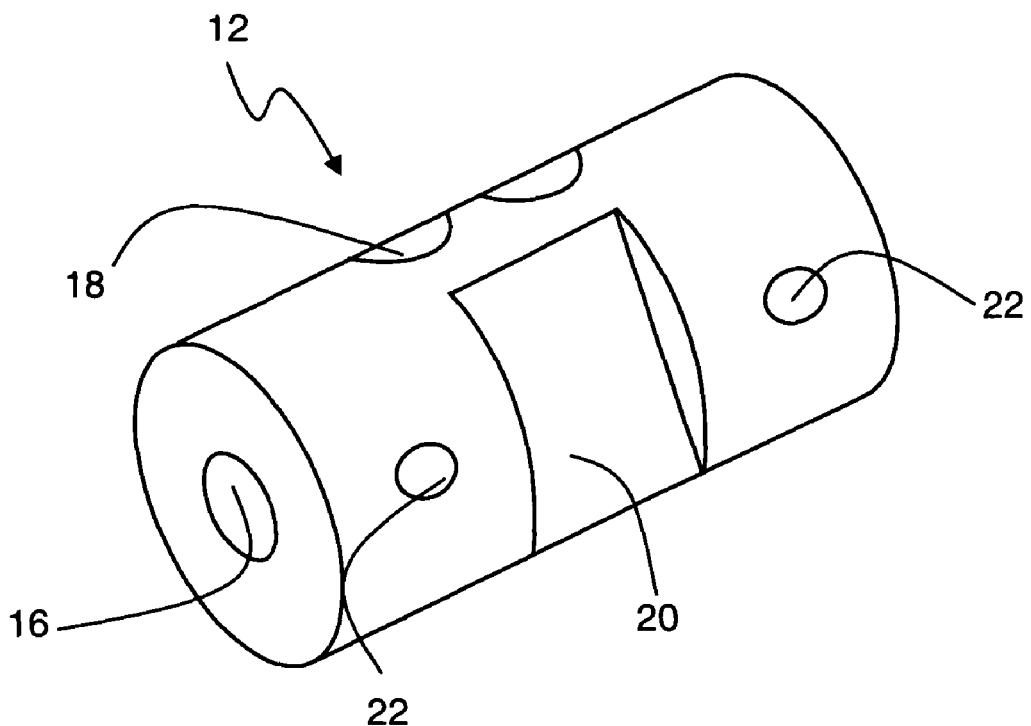
FIG. 2 is a perspective view of the inter-spinous spacer of the present invention shown in FIG. 1.
Figure 3:
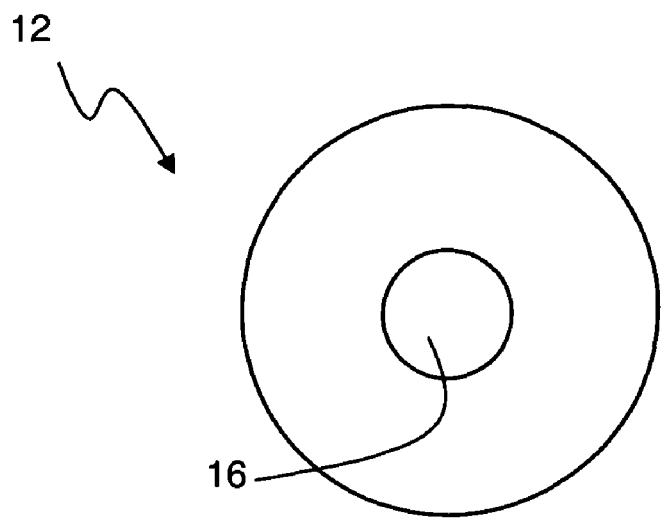
FIG. 3 is a side view of the inter-spinous spacer of the present invention as shown in FIG. 1.
Figure 4:
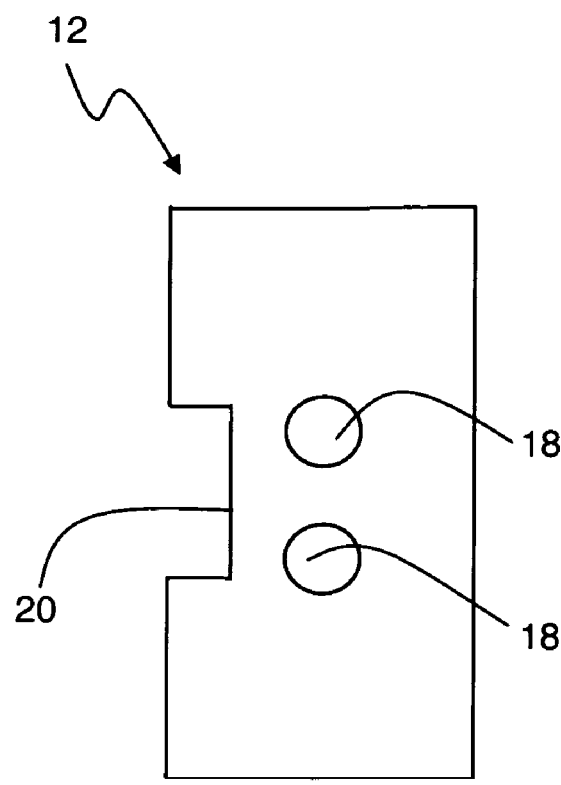
FIG. 4 is a front view of the inter-spinous spacer of the present invention as shown in FIG. 1.
Figure 5:
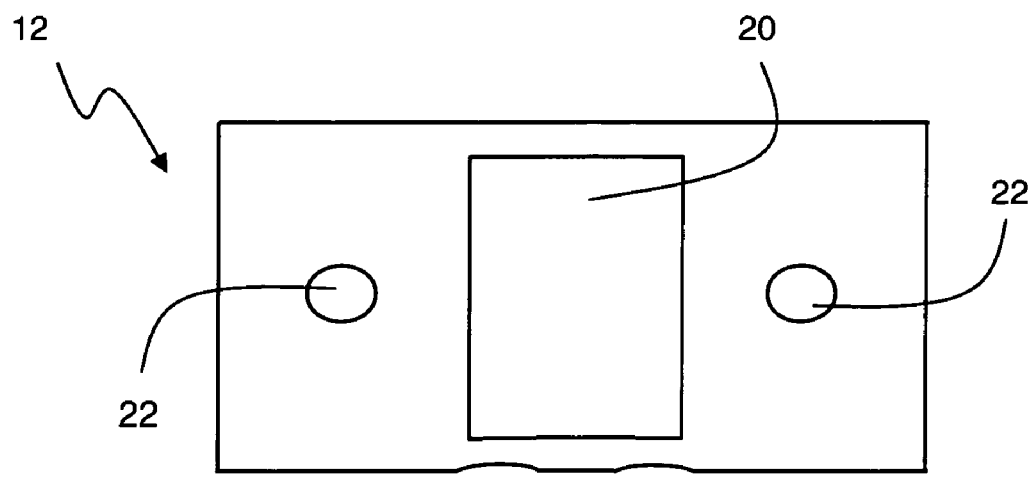
FIG. 5 is a top view of the inter-spinous spacer according to the present invention as shown in FIG. 1.
Figure 7:
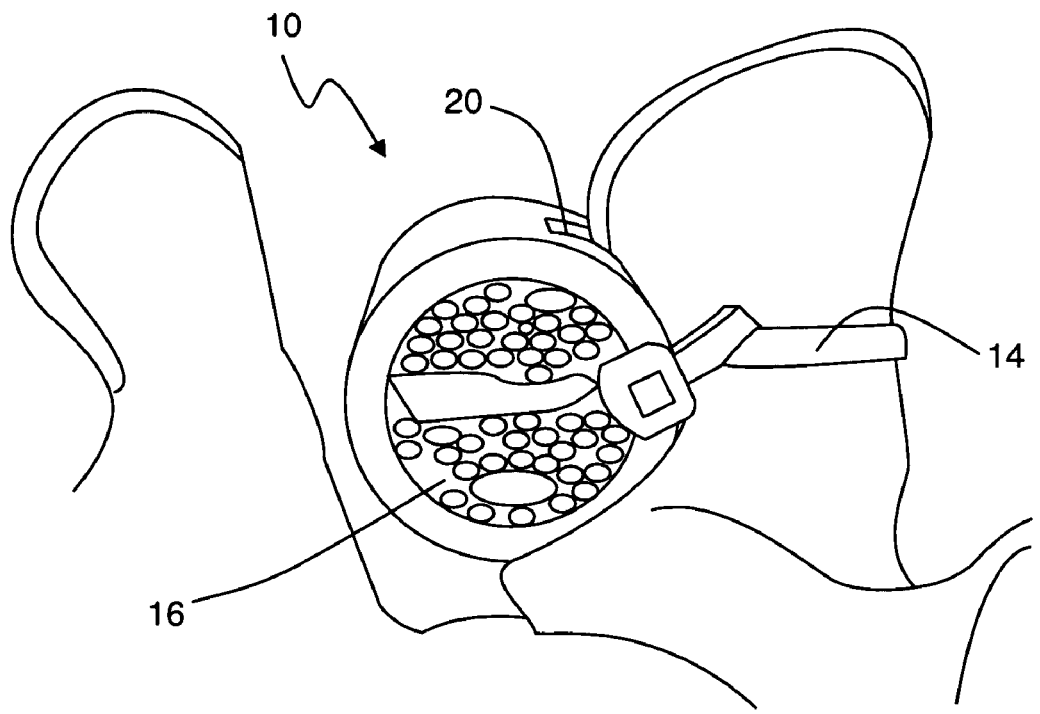
FIG. 7 is a perspective view illustrating the inter-spinous spacer shown in FIG. 1 with fusion-promoting materials disposed within an inner lumen according to one aspect of the present invention.

As depicted in FIGS. 2-3, the main chamber 16 extends through the lateral sides of the spacer 12. The main chamber 16 may be provided in any of a variety of suitable shapes in addition to the generally cylindrical shape shown, including but not limited to a generally oblong, triangular, rectangular shape and/or combinations thereof. The main chamber 16 may be dimensioned to receive fusion inducing materials 32, as best illustrated in FIG. 7. Again, such fusion inducing materials may include, but are not necessarily limited to BMP1, 2, 3, 4, 5, 6, 7, 8, 9, 10, 11, 12, 13, 14 . . . n, demineralized bone matrix, allograft cancellous bone, autograft bone, hydroxy appetite, coral and/or other highly porous substance. The fusion inducing materials may be packed into main chamber 16 before and/or after fixing spacer 10 to the spinous process. The pair of insertion tool apertures 18 may be located on either the posterior or anterior side of the spacer 12 and extend a portion of the way through the spacer 12. The fusion notch 20 includes a slot or indent to receive a portion of an upper spinous process or other vertebral feature to enhance fusion. The notch 20 may be located generally on the top surface towards the middle portion of the spacer 12. The notch 20 helps center the spacer 12 relative to the superior spinous process.

Figure 8:
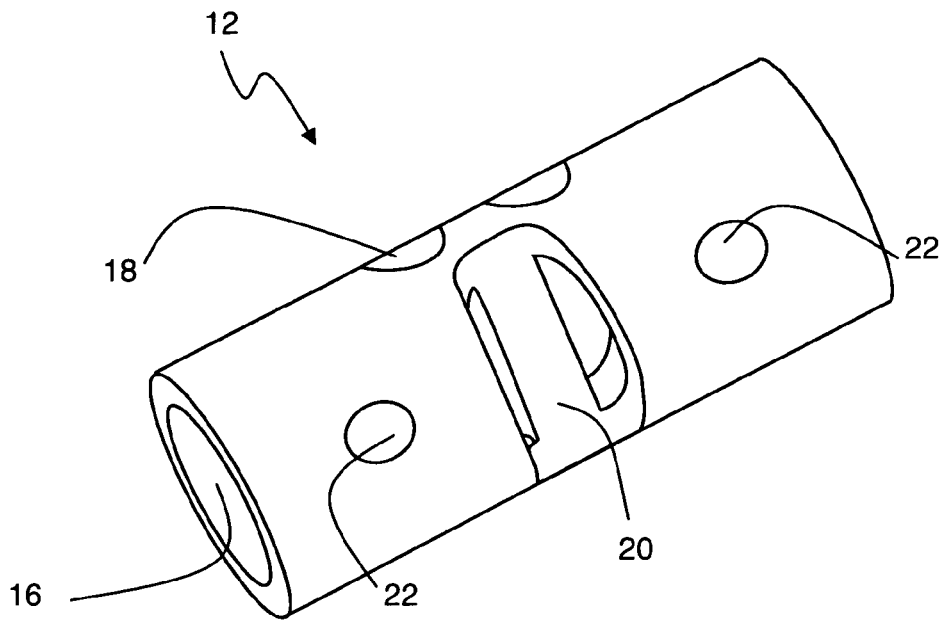
FIG. 8 is a perspective view of an inter-spinous spacer according to a second embodiment of the present.
Figure 9:
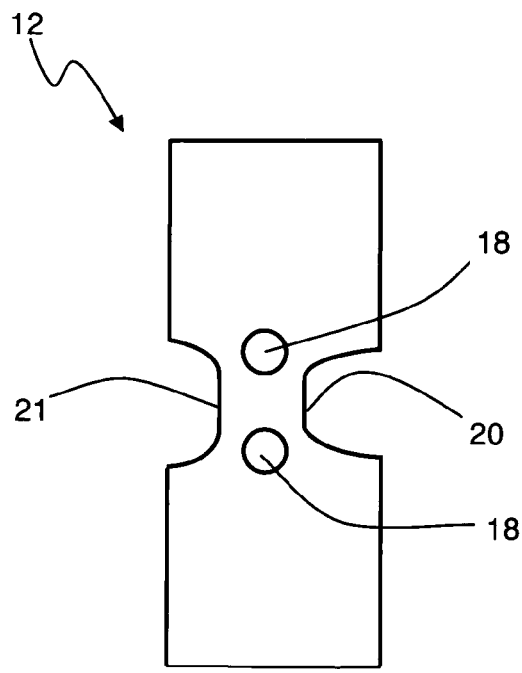
FIG. 9 is a side view of the inter-spinous spacer according to the present invention as shown in FIG. 8.
Figure 10:
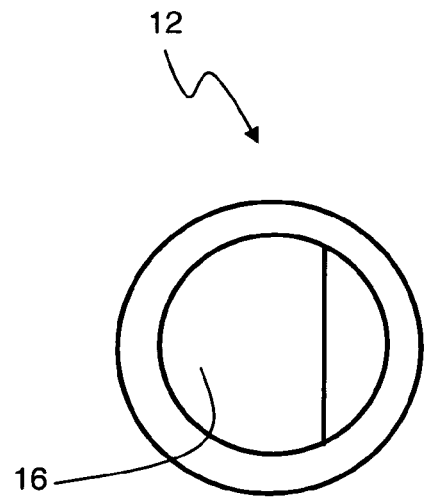
FIG. 10 is an end view of the inter-spinous spacer according to the present in invention as shown in FIGS. 8-9.

According to another embodiment, shown in FIGS. 8-10, the spacer 12 may be provided with a second notch 21 opposite the fusion notch 20. The second notch 21 is capable of resting on the inferior spinous process during use, which may assist in maintaining the spacer 12 in a fully centered position relative to the inferior spinous process. As best shown in FIG. 8, the fusion notch 20 may be further provided with slots 23 extending into the main chamber 16. When the spacer 12 is coupled to the superior spinous process, these slots 23 will establish direct communication between the fusion-inducing compounds provided within the main chamber 16 and the lower aspect of the superior spinous process, which advantageously augments the ability of the spacer 12 to fuse to the superior spinous process (particularly if the spacer 12 is constructed of non-bone materials).

Figure 6:
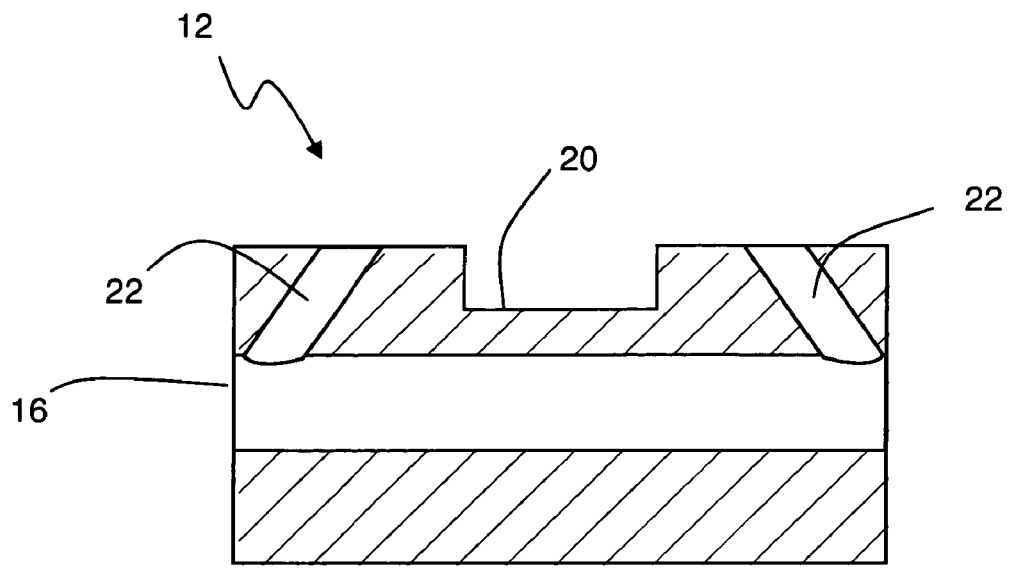
FIG. 6 is a cross-sectional view of the inter-spinous spacer of the present invention as taken through lines A-A of FIG. 5.

As best shown in FIG. 6, the tether lumens 22 each extend at an angle through the top surface of the spacer 12 and into the main chamber 16. Each tether lumen 22 may be provided in any of a variety of suitable shapes in addition to the cylindrical shape shown, including but not limited to oblong, triangular, rectangular and/or any combination thereof. The tethers 14, 15 may comprise any number of suitable materials and configurations, including but not limited to wire, cable, suture (permanent and/or bioresorbable), allograft tissue and/or other single or multi-filament member. Suture thread may include any number of components capable of attaching to a spinous process, including but not limited to ordinary suture threads known to and used by those skilled in the art of wound closure. Suture thread may be of any length necessary to effectively fuse the spacer 12 to the particular spinous process.

The spacer 12 according to the present invention may be constructed of allograft bone and formed in a generally cylindrical shape. The spacer 12 of the present invention may be provided in any number of suitable shapes and sizes depending upon a particular patient and the shape and strength characteristics given the variation from cadaver to cadaver. The spacer 12 may be dimensioned for use in the cervical and/or lumbar spine without departing from the scope of the present invention. The spacer 12 may be dimensioned, by way of example only, having a length ranging between 6-20 mm and a height ranging between 20-25 mm.

When constructed from allograft, the spacer 12 may be manufactured according to the following exemplary method. A belt sander may first be used to reduce any high spots or imperfections to standardize the shape of the bone. Cut the allograft bone to length using the band saw. Remove the cancellous material from the inner canal to create the main chamber 16. Using calipers, measure the struts and create a size distribution of spacers 12. Machine the insertion tool apertures 18. Set-up a standard vice for holding the implant across its width on the mill. Use a ³⁄₃₂" ball end mill to create the insertion tool apertures 18 (same as cervical allograft implant). Insert the spacer 12 into the vice and tighten. Calculate the centerline of the 20 or 25 mm long spacer 12. Create the holes 2.26 mm away from each side of the centerline (4.52 mm hole to hole distance). Create a notch 22 for the spinous process. Set-up the cervical allograft holding fixture that uses the insertion tool apertures 18 and vice to hold the spacer 12 across its width on the mill. Use a ¼" flat end mill to create the notch 22. Calculate the centerline of the 20 or 25 mm long spacer 12. Insert the spacer 12 onto the fixture using the insertion tool apertures 18 and tighten the vice. This automatically verifies the correct sizing/spacing of the insertion tool apertures 18. Measure the spacer 12 height. Calculate the cut depth to create the desired spacer 12 size. Cut the flat on the spacer 12 to the desired depth. Remeasure the spacer 12 to insure proper cut depth. Drill the angled lumens 22 in face of spacer 12. Remove the spacer 12 from the cervical allograft fixture and tighten into the standard vice. Using a battery powered or corded drill with a ¹⁄₁₆" drill bit, drill through the front face to the canal on both sides. Belt sand the face if needed to create a flat surface for the drill bit to engage the spacer 12.

Figure 11:
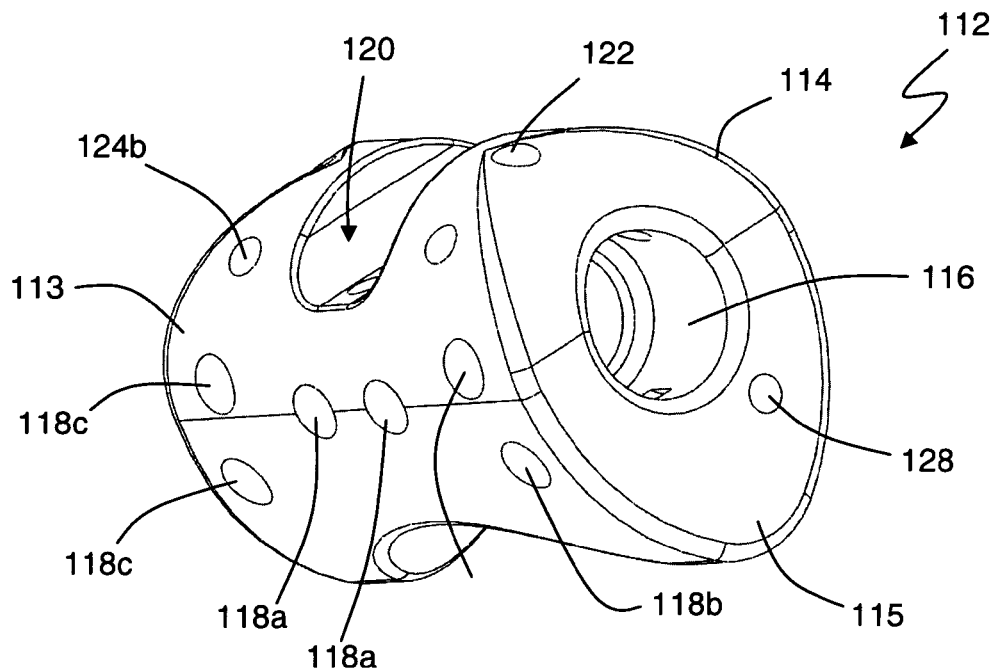
FIG. 11 is a perspective view of an inter-spinous spacer according to a third embodiment of the present invention in use affixed to a superior spinous process of a human spine.

Turning now to FIG. 11 there is shown in perspective view an example of a spacer 112 according to another embodiment of the present invention. Spacer 112 includes a posterior side 113, anterior side 114, lateral sides 115, a main chamber 116, and a fusion notch 120. Spacer 112 is further provided with a plurality of apertures including, but not necessarily limited to, three pairs of insertion tool apertures 118a, 118b, and 118c, tether lumens 122, and secondary fusion apertures 124b.

Figure 12:
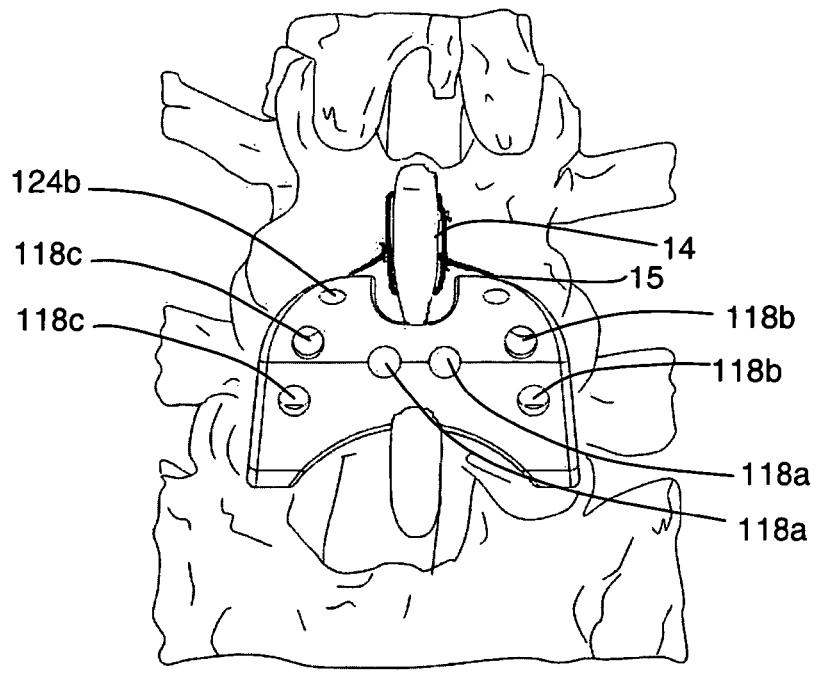
FIG. 12. is a frontal view of the inter-spinous spacer according to the present in invention as shown in FIG. 11, in place in between the two spinous processes.
Figure 13:
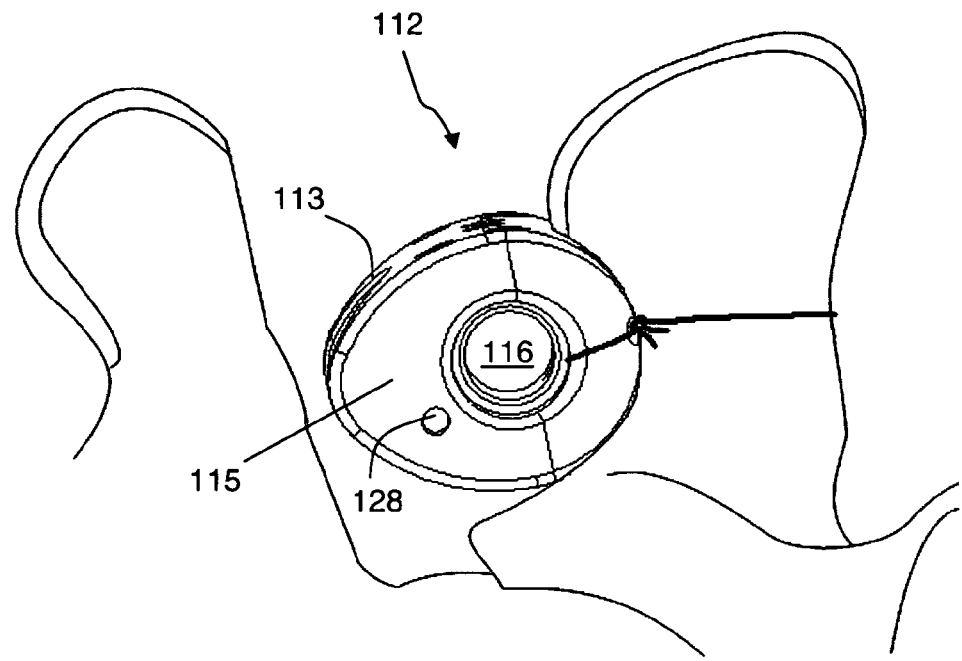
FIG. 13. is a side view of the inter-spinous spacer according to the present in invention as shown in FIG. 11, in place in between the two spinous processes.
Figure 14:
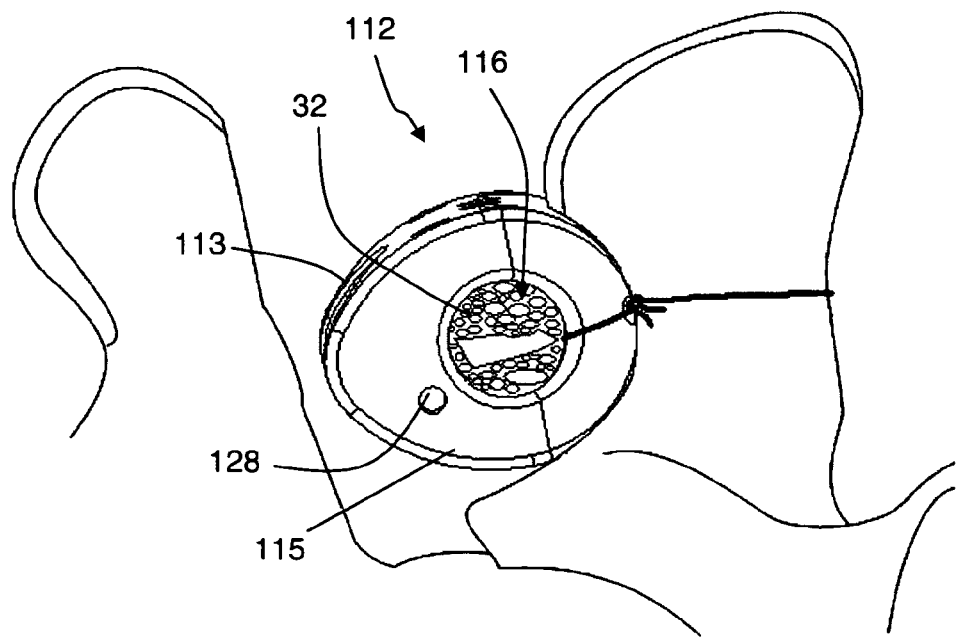
FIG. 14. is a side view of the inter-spinous spacer according to the present in invention as shown in FIG. 11, in place in between the two spinous processes with fusion inducing material packed inside.

FIGS. 12-14 depict spacer 112 in use in the inter spinous process space of a patient. Spacer 112 is designed to fit between a superior spinous process and an inferior spinous process and may be dimensioned in any number of suitable shapes and sizes to accomplish this. The spacer 112 may be positioned in any of the cervical, thoracic, and/or lumbar spine and sizes may vary accordingly. When in position, a properly sized spacer 112 distracts the inter spinous process space, restoring the foraminal height in stenotic patients and indirectly decompresses the intervertebral space. By way of example only, spacer 112 may be dimensioned having a length ranging between 6-20 mm and a height ranging between 20-25 mm.

Spacer 112 is preferably constructed of non-bone material. Suitable non-bone materials may include, but are not necessarily limited, to polyaryletherketone (PEEK) and polyaryletherketoneketone (PEKK). Numerous advantages may be gained by constructing spacer 112 out of materials such as PEEK and PEKK. The stiffness properties of PEEK and PEKK closely match that of bone. This reduces substantially the likelihood that the spinous process will remodel around spacer 112 causing a re-narrowing of the foraminal height and potentially resulting in revision surgeries. PEEK and PEKK are also substantially radiolucent which allows for improved post operative visualization of fusion between the implant and the superior spinous process. Finally, by using the non bone material with strategically placed apertures, fusion may be confined to areas where it is useful. By way of example only, spacer 112 may include fusion apertures only along the top (and potentially posterior side 113) such that fusion occurs only between the superior spinous process and spacer 112. In this manner, extension is limited without disadvantageously limiting flexion as well.

As depicted in FIG. 13, the main chamber 116 extends through the lateral sides 115 of the spacer 112. Main chamber 116 may be provided in any of a variety of suitable shapes in addition to the generally cylindrical shape shown, including but not limited to a generally oblong, triangular, rectangular shape and/or combinations thereof. Main chamber 116 may be dimensioned to receive fusion inducing materials 32, as best illustrated in FIG. 14. Again, such fusion inducing materials may include, but are not necessarily limited to BMP1, 2, 3, 4, 5, 6, 7, 8, 9, 10, 11, 12, 13, 14 . . . n, demineralized bone matrix, allograft cancellous bone, autograft bone, hydroxy appetite, coral and/or other highly porous substance. The fusion inducing materials 32 may be packed into main chamber 16 before and/or after fixing spacer 10 to the spinous process. The fusion inducing material 32 packed within main chamber 16 may communicate openly with the superior spinous process through any of the insertion tool apertures 118a, 118b, 118c, fusion apertures 124, and/or tether apertures 122. Through this communication, fusion may occur from the superior spinous process into the main chamber 116, permanently fixing spacer 112 in position.

Figure 15:
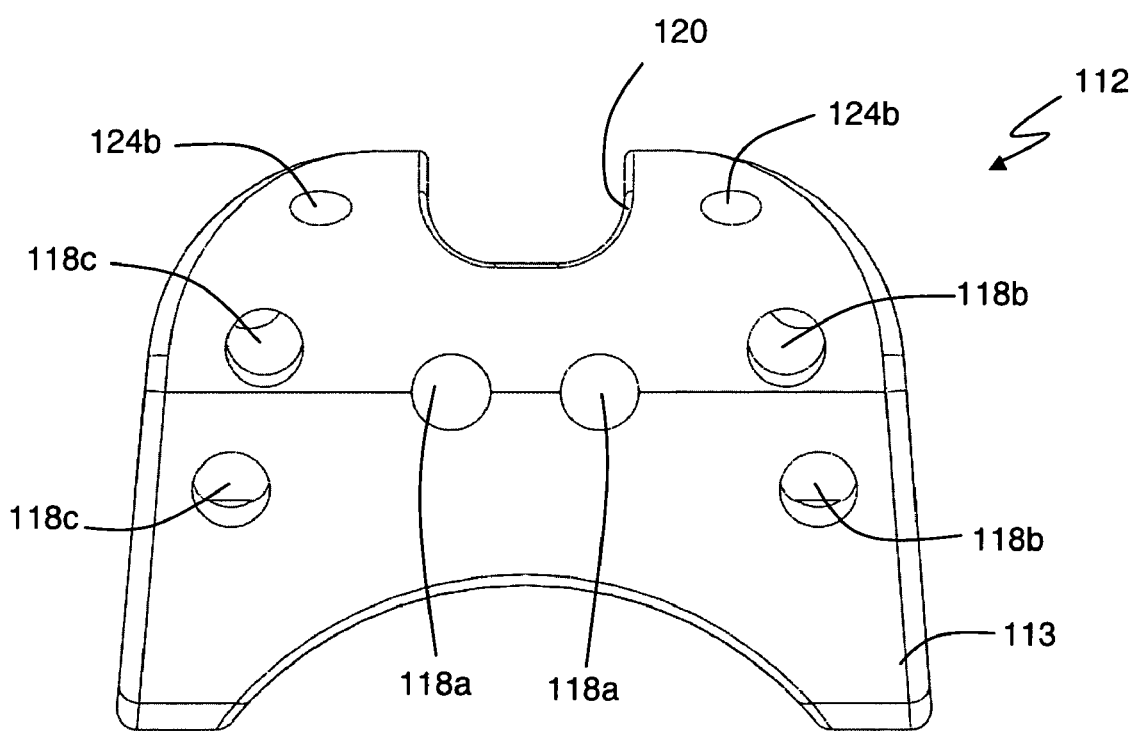
FIG. 15 is a front view of the inter-spinous spacer according the present invention as shown in FIG. 11.
Figure 16:
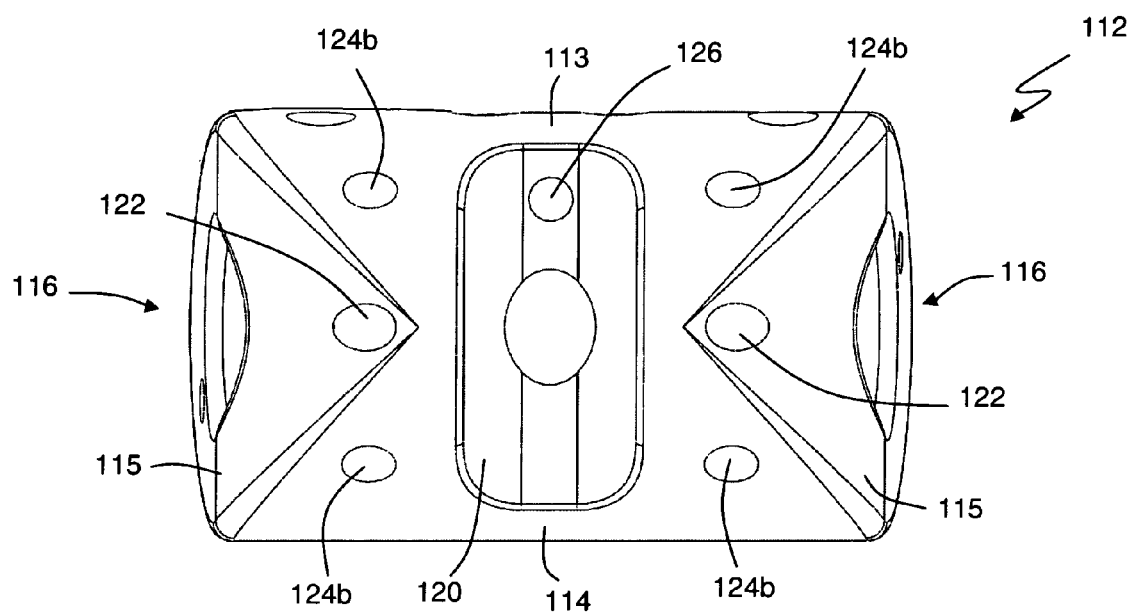
FIG. 16 is a top view of an inter-spinous spacer according the present invention as shown in FIG. 11.

With reference to FIGS. 15-19, the various features of spacer 112 will now be described according to one preferred embodiment. FIG. 16 is a view of the top of spacer 112. Fusion notch 120 may be located generally on the top surface towards the middle portion of the spacer 112. Fusion notch 120 generally comprises a slot or indent dimensioned to receive an inferior portion of a superior spinous process. The notch 120 helps center the spacer 112 relative to the superior spinous process and may assist in limiting side-to-side motion of spacer 112 prior to fusion. Fusion notch 120 includes main fusion aperture 124a. Main fusion aperture 124a extends into main chamber 116 and is the main avenue for fusion between main chamber 116 and the superior spinous process. Secondary fusion apertures 124b may be located along the top of spacer 112 near the four corners of fusion notch 120 and extend into main chamber 116. Secondary fusion apertures 124b may provide additional routes for fusion to the superior spinous process. Tether apertures 122 may be located along the top center of spacer 112 near either side of fusion notch 120. Tether apertures 122 are dimensioned to receive tethers 14, 15 to temporarily fix spacer 112 in position until fusion to the superior spinous process occurs, permanently fixing spacer 112 in place.

Main fusion aperture 124a, secondary fusion apertures 124b, and tether apertures 122 may each be provided in any of a variety of shapes in addition to the generally circular shapes shown, including but not necessarily limited to, generally square, rectangular, oblong, triangular, and/or any combination thereof.

FIG. 15 illustrates the posterior side 113 of spacer 112. The posterior side 113 may include 3 separate pairs of insertion tool apertures 118a, 118b, and 118c. As will be described in more detail below, having three pairs of insertion apertures allow different insertion approaches to be utilized without needing to make available separate tools and/or spacers with alternate aperture configurations. Insertion tool apertures extend into main chamber 116 and may serve as additional fusion routes after insertion, this may further solidify and strengthen the fusion between the superior spinous process and spacer 112.

Figure 17:
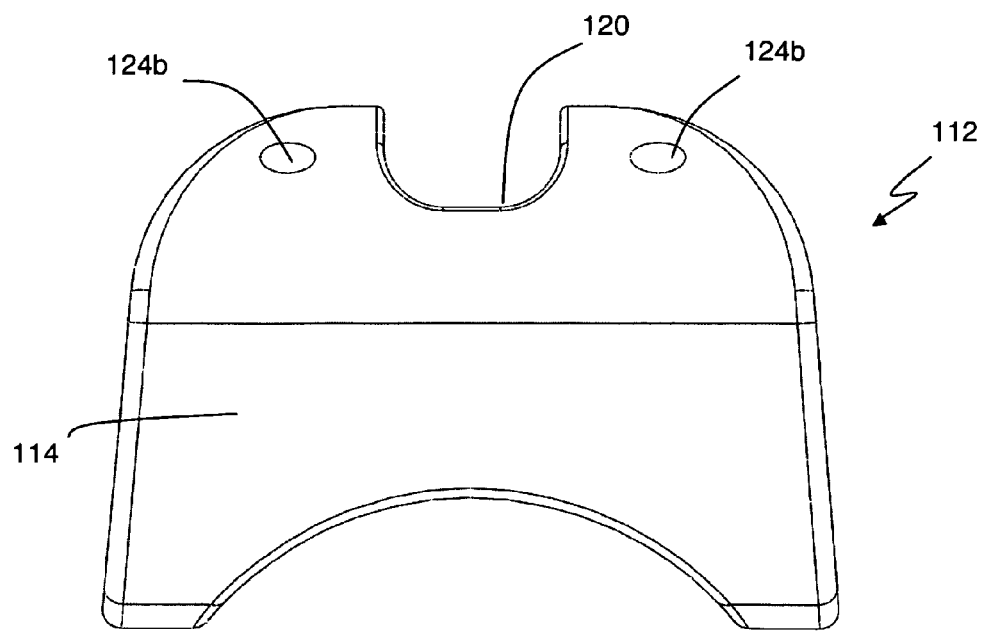
FIG. 17 is a back side view of an inter-spinous spacer according the present invention as shown in FIG. 11.
Figure 18:
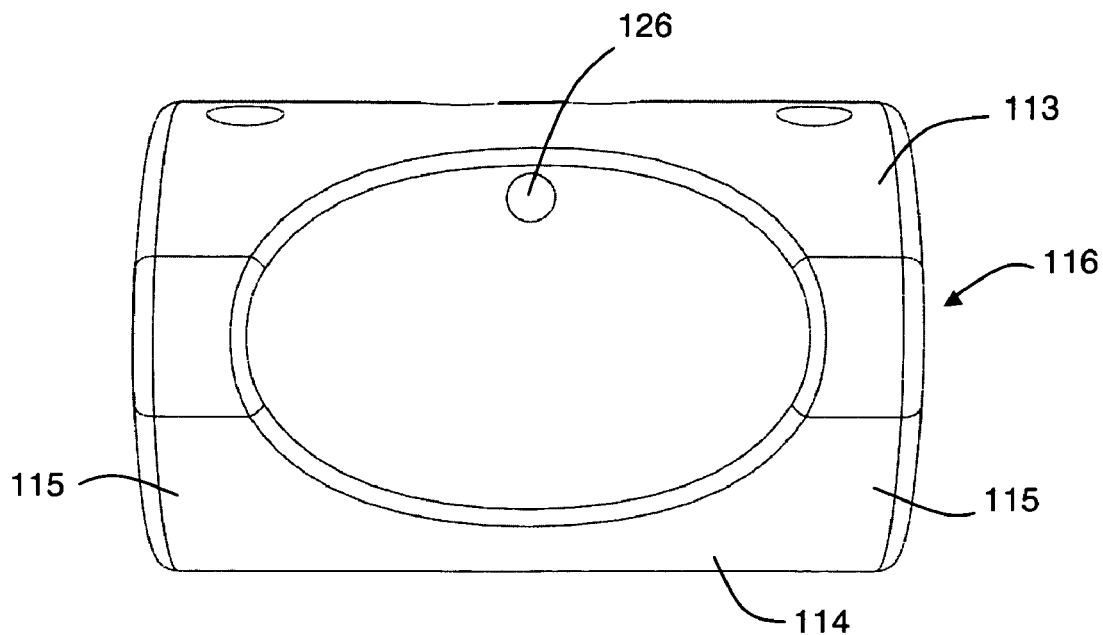
FIG. 18 is bottom view of an inter-spinous spacer according the present invention as shown in FIG. 11.
Figure 19:
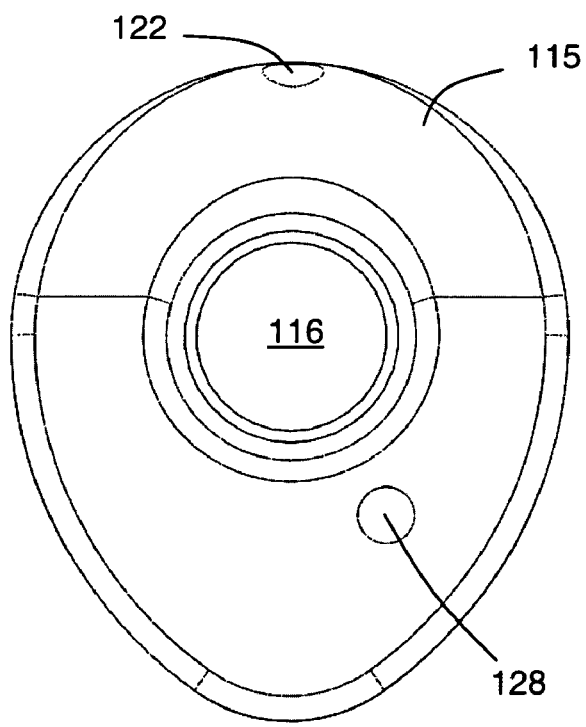
FIG. 19 is a side view of an inter-spinous spacer according the present invention as shown in FIG. 11.
Figure 20:
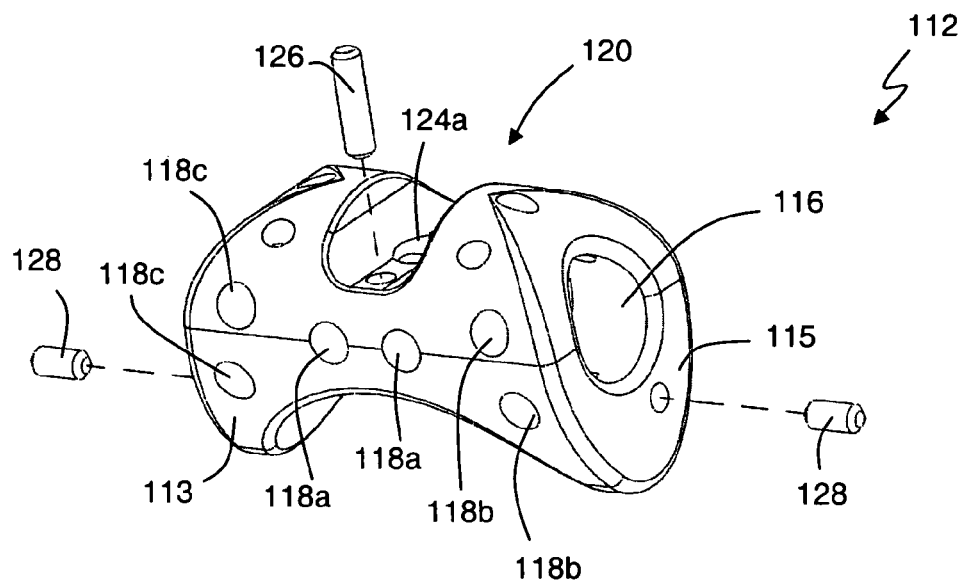
FIG. 20 is perspective view of an inter-spinous spacer according the present invention as shown in FIG. 11 including visualization markers.

FIG. 17 illustrates the anterior side 114 of spacer 112 and FIG. 18 illustrates the bottom of the spacer. The anterior side 114 is preferably free of any apertures (except, secondary fusion apertures 124b may be located near the top of spacer 112 on the anterior side). When positioned in the inter spinous process space, the anterior side 114 faces the spinal canal. Bone growth along the anterior side could potentially interfere with the spinal canal and the delicate neural tissue located inside, which could result in pain and/or further surgery for the patient. The lack of communication to main chamber 116 caused by the absence of apertures on the anterior side 114 advantageously prevents bone growth in the area. Likewise, the bottom of spacer 112 is also aperture free and does not communicate with main chamber 116. This advantageously prevents bone growth in the area and fusion to the inferior spinous process will not occur. Again, this allows the spinal segment to maintain flexion ability while still correcting the stenosis. The bottom of spacer 112 may preferably have a concave surface such that the distance from top to bottom of spacer 112 is greater neareast the lateral sides 115 and lesser near the center. The concave bottom may rest along the inferior spinous process and helps maintain spacer 112 in a centered position relative to the inferior spinous process. FIG. 19 illustrates again a lateral side 115 with main chamber 116 extending therethrough.

To assist in visualization of spacer 112, both during and after surgery, spacer 112 may include at least one marker. Preferably, spacer 112 includes a top marker 126 and two side markers 128. Markers 126, 128 may be comprised of biocompatible radio-opaque material, such as for example only, titanium (or other metals or polymers). Marker 126 may be positioned along the center of spacer 112 within fusion notch 120. Preferably marker 126 extends through spacer 112 down to the bottom surface. Markers 128 may be located in the lateral sides below main chamber 116. During and after placement of the spacer 112, markers 126 and 128 may be utilized to correctly orient spacer 112.

Figure 30:
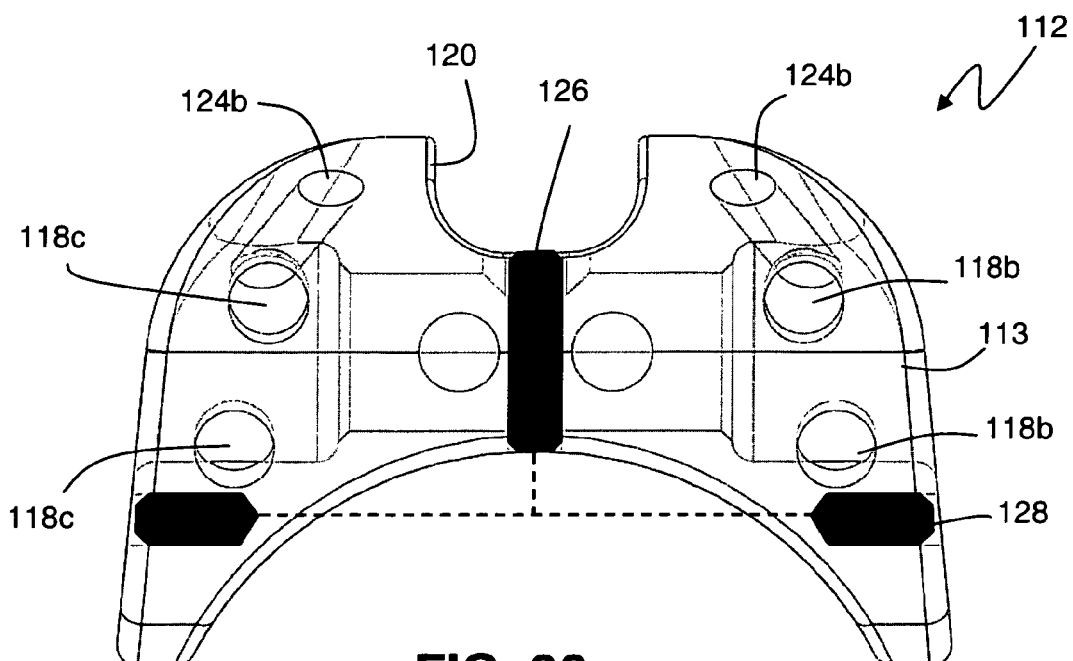
FIG. 30 illustrates a posterior fluoroscopy view taken during implantation of the inter-spinous spacer of FIG. 11 demonstrating the alignment of markers (including the formation of a "T") to aid in placement.
Figure 31:
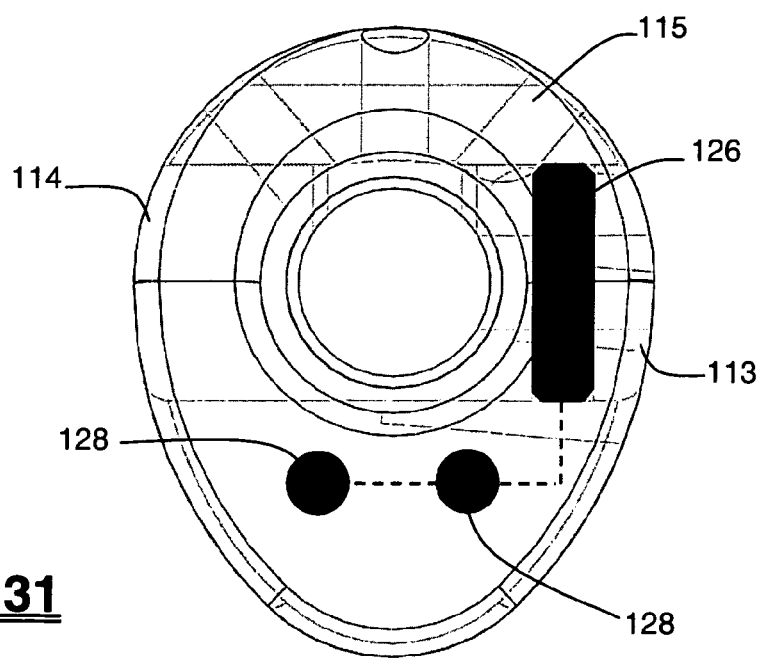
FIG. 31 illustrates a lateral fluoroscopy view taken during implantation of the inter-spinous spacer of FIG. 11 demonstrating the position of markers (including the formation of a backwards "L") to aid in placement.

Utilizing X-ray fluoroscopy and/or other suitable imaging techniques from the posterior (or the back of the patient) perspective of the spacer 112, the marker 126 situated in the center and extending from fusion notch 120 to the bottom surface should make a line between the superior spinous process and the inferior spinous process viewable on the fluoroscopy screen when the spacer 112 is properly positioned, as pictured in FIG. 30. Markers 128 should be positioned on each side of the superior and inferior spinous process in the inter spinous process space. Drawing an imaginary line between markers 128 and connecting that line to an imaginary line extending marker 126 to it should form an upside down "T" if properly positioned. From a lateral view, the depth of the spacer 112 in the interspinous space may be verified. Marker 126 runs along the posterior side 113 of spacer 112. One or both of markers 128 may be positioned in the lateral side 115 near the posterior side 113. In one embodiment, one marker 128 is positioned near the posterior side 113 and one marker 128 may be positioned near the anterior side 114. On a lateral fluoroscopy view taken during surgery the position of the markers 126 and 128 may be viewed in relation to the posterior end of the spinous processes and the more anterior vertebral elements to ensure spacer 112 is neither too far anteriorly nor to far posoteriorly. Drawing an imaginary line between markers 128 and connecting that line to an imaginary line extending marker 126 to it should form a backwards "L" if properly positioned, as pictured in FIG. 31.

Figure 21:
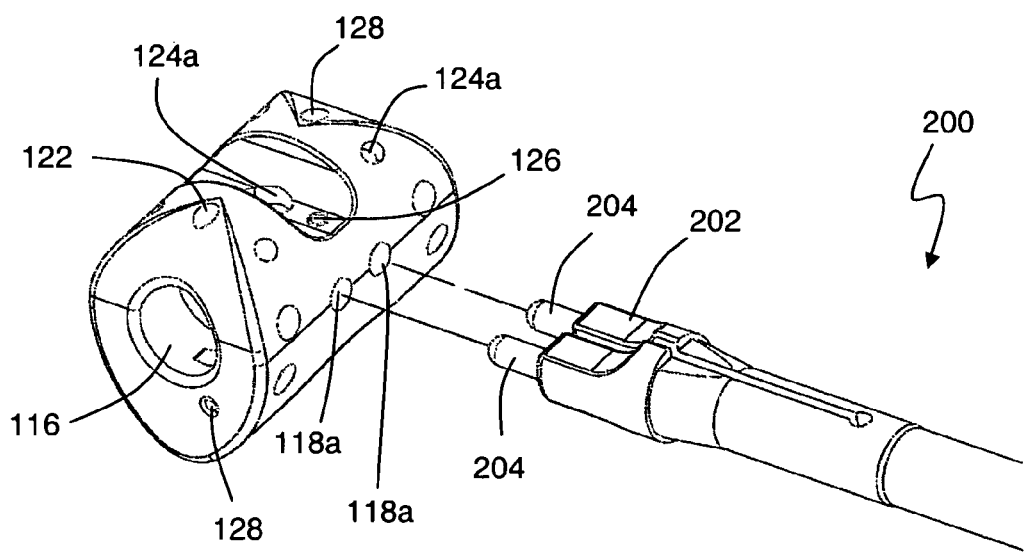
FIGS. 21-23 illustrate an exemplary insertion tool in use with the inter-spinous spacer of FIG. 11, according to one embodiment of the present invention.
Figure 22:
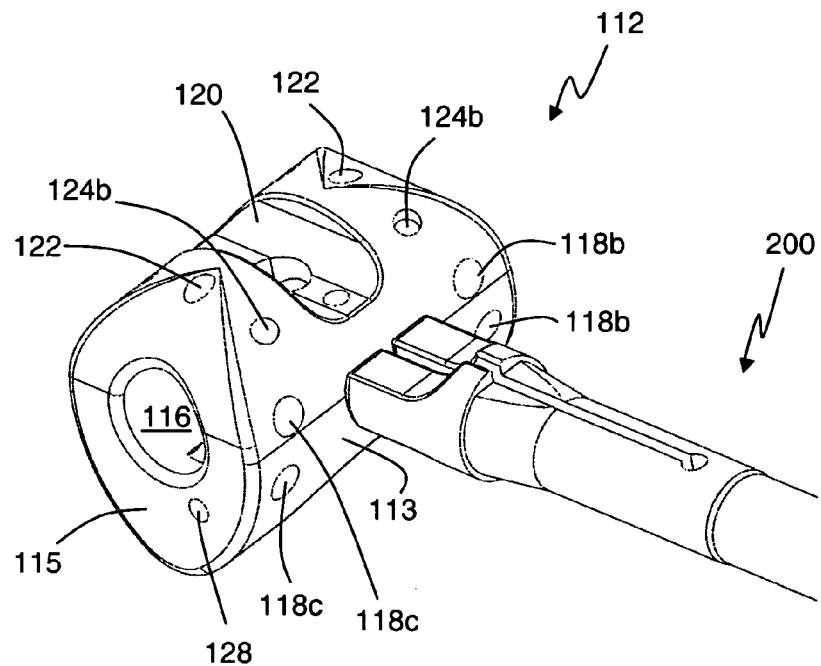
Figure 23:
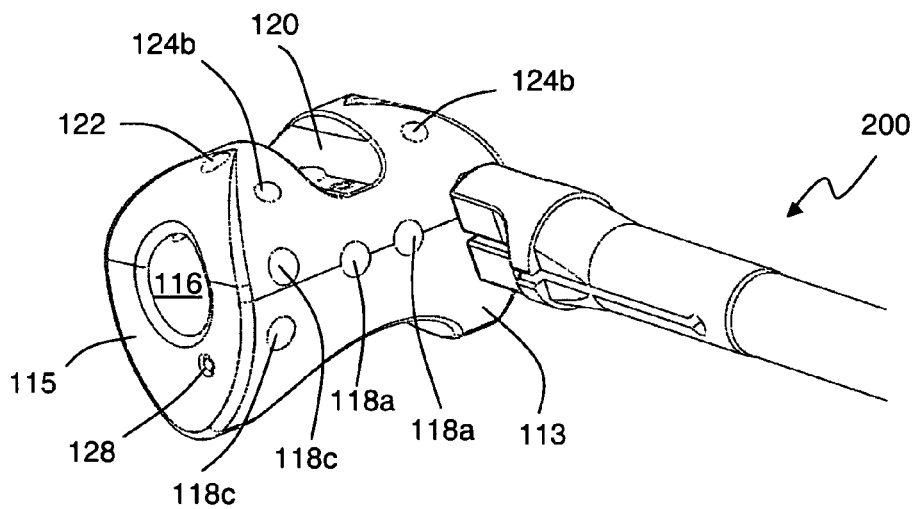
Figure 24:
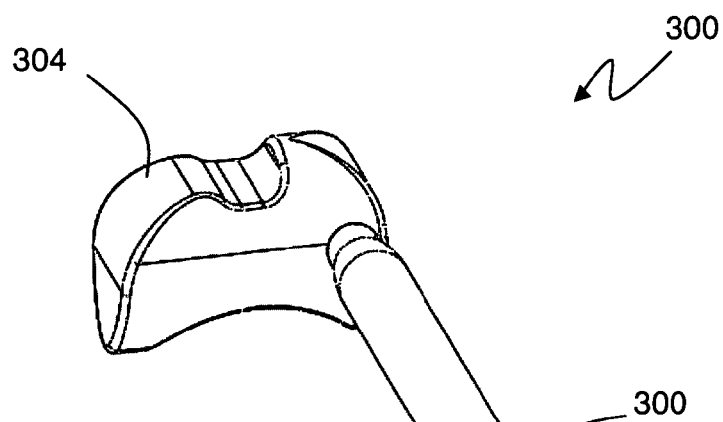
FIGS. 24-27 illustrate an exemplary sizer tool for use when implanting the inter-spinous spacer as shown in FIG. 11; according one embodiment of the present invention.
Figure 25:
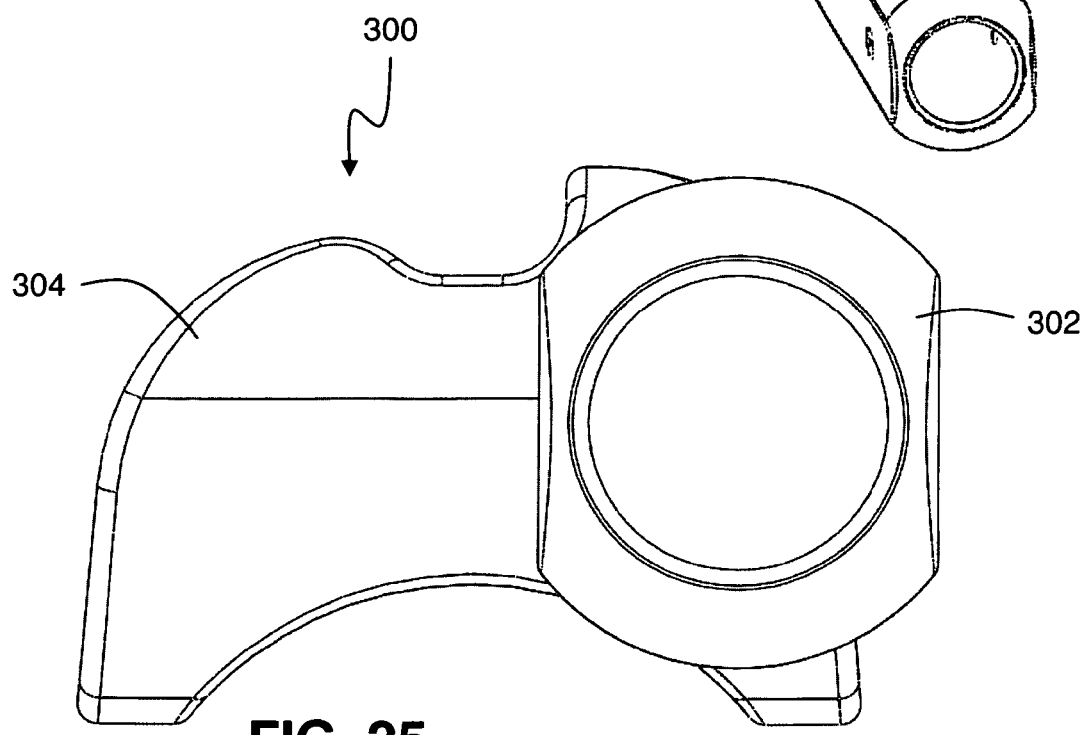
Figure 26:
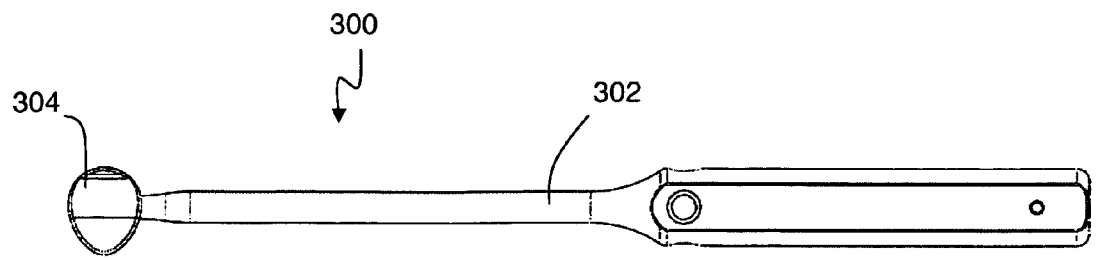
Figure 27:
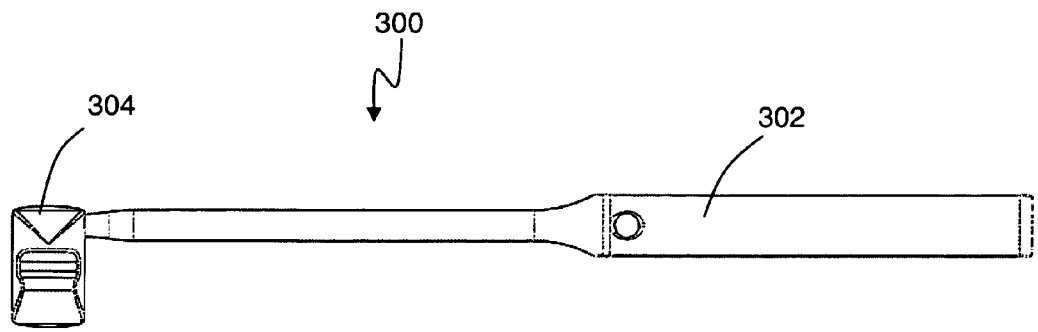

The spinal apparatus 10 of the present invention may be introduced into a spinal target site through the use of any of a variety of suitable instruments having the capability to releasably engage the spacer 12, 112. In a preferred embodiment, the insertion tool permits quick, direct, accurate placement of the spacers 12, 112 between an upper and lower spinous process. An exemplary insertion tool is shown and described in commonly owned U.S. Pat. No. 6,923,814 entitled "System and Method for Cervical Fusion," which is expressly incorporated by reference as if set forth fully herein. FIGS. 21-23 depict an exemplary insertion tool 200 for use with spacers 12, 112. At a distal end 202, insertion tool 200 includes a pair of prongs 204 dimensioned to engage insertion apertures 18 and 118a, 118b, 118c such that spacer 12, 112 becomes temporarily attached to the distal end 202 for insertion. Insertion apertures 118a are aligned laterally in the center of spacer 112 such that spacer 112 and insertion tool 200 mate at approximately the center point of the spacer, as pictured in FIG. 22. This configuration may be advantageous if approaching the inter spinous process space from a directly posterior approach. Insertion apertures 118*b* and 118*c* are aligned vertically near opposite sides of spacer 112, such that spacer 112 and insertion tool 200 mate at near the selected side, as illustrated in FIG. 23 (shown with tool 200 attached to insertion apertures 118*b*). This configuration may be advantageous if approaching from a more lateral direction.

In order to use the spinal apparatus 10 of the present invention in a treatment of spinal stenosis, a clinician must first designate the appropriate spacer size 12, 112. A clinician can utilize the spinal apparatus 10 in either an open or minimally invasive spinal fusion procedure. In either type of procedure, a working channel would be created in a patient that reaches a targeted spinal level. After the creation of the working channel, the interspinous space would be prepared. After preparation a sizer instrument is used to determine the appropriate size of the spacer 12, 112. One exemplary sizer instrument 300 is illustrated by way of example only in FIGS. 24-27. Sizer instrument 300 includes a handle portion 302 and an implant portion 304. Handle portion 302 may be configured in any variety of suitable shapes and sizes. Implant portion 304 may be provided in a variety of sizes matching the various sizes of spacer 112. As pictured, sizer implant may be proved in an asymmetrical shape where the side opposite the handle 302 has a lesser height than the side to which handle 302 is attached. This may allow the implant portion 304 to be rotated into position with minimal interference from the spinous process. Although it is not shown, it is conceived that spacer 112 may also be provided in this asymmetrical fashion.

Preparation of the inter spinous process space includes perforating the interspinous ligament between the superior and inferior spinous processes. The supraspinous ligament may preferably be left intact and distracted out of the way if necessary. A key part of the preparation includes abrading the inferior portion of the superior spinous process where it will communicate with the fusion inducing materials 32 packed in the main chamber 16, 116. Abrading removes the hard cortical bone from the inferior surface of the superior spinous process and leaves bleeding bone which is better adapted for fusion. As new bone generates to heal the abraded portion it may grow into the main chamber 16, 116, fixing spacer 12, 112 to the superior spinous process.

Figures 28, 29:
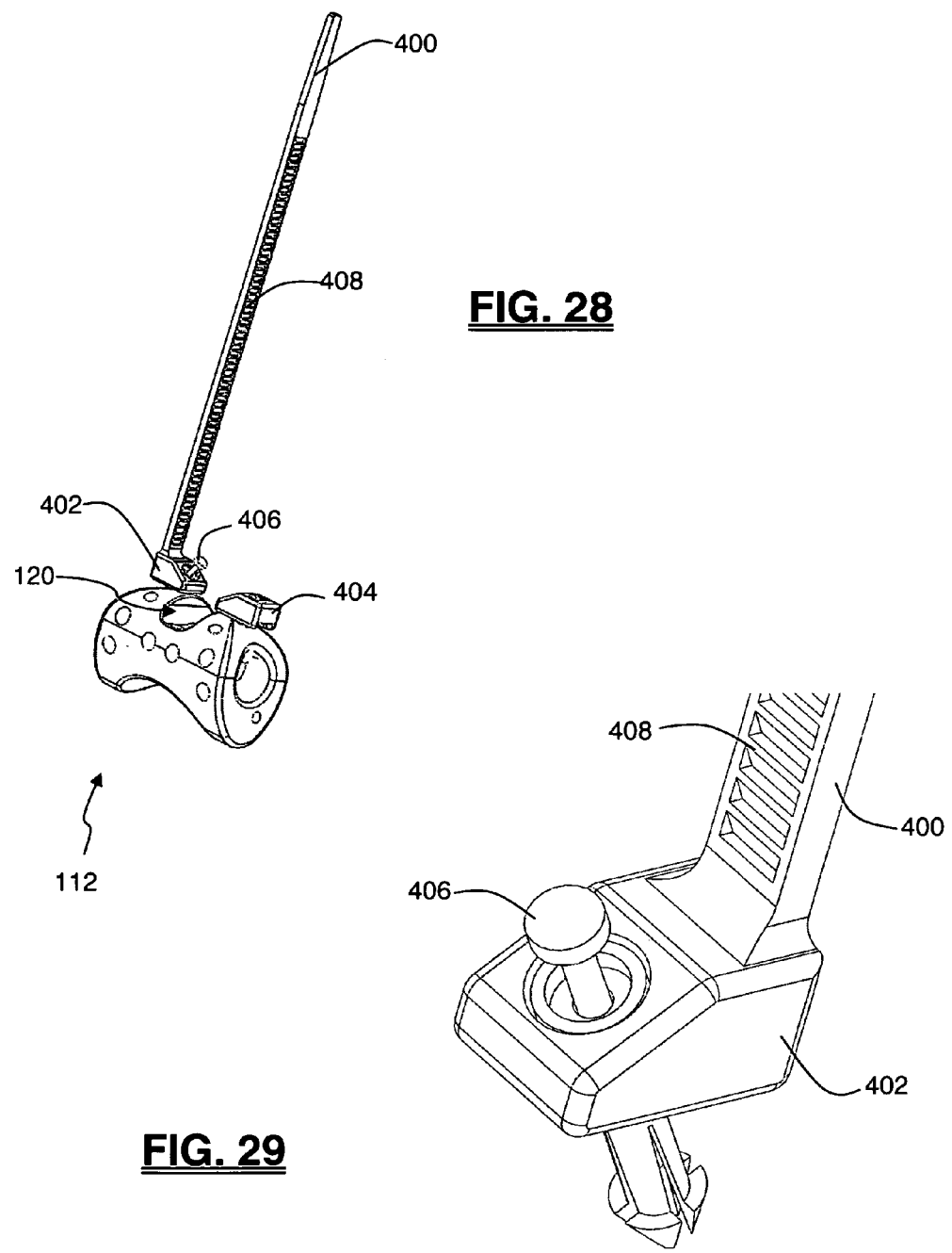
FIGS. 28-29 illustrate an alternate attachment device for use with the inter-spinous spacer shown in FIG. 11 according to an alternate embodiment of the present invention.

In one embodiment described above the spacer 12, 112 is held in position with tethers 14, 15 attached to the spinous process through tether lumen 22, 122. According to an alternate embodiment, pictured by way of example only in FIGS. 28-29 an alternate securing mechanism may be used to fix spacer 12, 112 in place. The alternate securing mechanism includes a zip cable 400 and a pair of locking bases 402, 404. Base 402 may be integral with cable 400. Base 402 is positioned on the top of spacer 12, 112 next to the fusion notch 20, 120 and fixed to the spacer 12, 112 via tether apertures 22, 122. Base 402 is positioned over tether aperture 22, 122 and a locking pin 406 is inserted through the base into tether aperture 22, 122. The step is repeated for base 404 on the opposite side of the fusion notch 20, 120. Once both bases are in position and the spacer 12, 112 is positioned between the spinous processes, the zip cable 400 may be wrapped around the superior spinous process and fed through the opposing base 404. Teeth 408 on the cable 400 prevent cable 400 from loosening and thus holds the spacer 12, 112 in place for fusion to occur. Any of a variety of suitable materials may be used to form the zip cable 400, bases 402, 404, and locking pins 406. In one exemplary embodiment the cable 400 and bases 402, 404 are comprised of nylon and the locking pins 406 are comprised of titanium.

When the spacer 12, 112 is positioned and inserted into the prepared space between the spinous processes it forces the spinous processes apart. The spine flexes as the spinous processes are forced apart and the neuroforamina and the spinal canal are enlarged as the spine is flexed. The spinal apparatus 10 holds the vertebrae in a flexed position, preventing extension but advantageously allowing flexion.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the spirit and scope of the invention as defined herein.

What is claimed is:

1. A method for treating spinal stenosis, comprising:
    gaining access to an inter spinous process space between a superior spinous process and an inferior spinous process;
    abrading a portion of the superior spinous process;
    inserting an implant in the inter spinous process space, the implant having opposing lateral sides, and anterior side, and a posterior side, wherein said anterior side includes at least one pair of apertures for releasably engaging an insertion tool;
    verifying the position of the implant by observing on a radiographic image the position of three-radiopaque markers embedded in the implant, a first of the radio-opaque markers being positioned at the center of the implant in a superior-inferior orientation, a second of the radio-opaque markers being positioned in one of said lateral sides and in an anterior aspect of the implant, and a third of the radio-opaque markers being positioned in the opposite lateral side and in a posterior aspect of the implant; and
    coupling the implant to the superior spinous process.

2. The method of claim 1, wherein the implant includes at least one aperture to allow bone to grow into the implant.

3. The method of claim 2, wherein the implant includes an interior chamber in communication with the at least one aperture and comprising the additional step of packing the chamber with fusion inducing material one of before and after coupling the implant to the spinous process.

4. The method of claim 3, wherein the fusion inducing material includes any of Bone Morphogenic Protein, demineralized bone matrix, allograft cancellous bone, autograft bone, hydroxyl appetite, and coral.

5. The method of claim 3, wherein the at least one aperture is positioned such that it contacts the superior spinous process.

6. The method of claim 2, wherein the implant includes a main aperture to allow bone growth into the implant and at least one secondary aperture to allow bone growth in the implant.

7. The method of claim 2, wherein the implant includes a notch dimensioned to receive a portion of the superior spinous process and comprising the additional step of fitting the portion of the superior spinous process into the notch during insertion.

8. The method of claim 7, wherein the at least one aperture for allowing bone to grow into the implant is positioned within the notch.

9. The method of claim 7, wherein a second notch is positioned on a bottom of the implant and interacts with the inferior spinous process.

10. The method of claim 1, wherein the implant includes an aperture for releasably attaching an insertion tool and comprising the additional step of attaching the insertion tool to the implant prior to insertion.

11. The method of claim 10, wherein in the insertion tool includes a pair of prongs that engage a pair of insertion apertures dimensioned to receive the prongs.

12. The method of claim 11, wherein the implant includes at least two pairs of apertures for engaging the insertion instrument and comprising the additional step of choosing which pair of apertures to engage.

13. The method of claim 1, wherein the implant is coupled to the superior spinous process with at least one of a tether, screw, clamp, and zip cable.

14. The method of claim 13, wherein the tether is one of a wire, cable, suture, and allograft tissue.

15. The method of claim 14, wherein the implant includes at least one aperture dimensioned to receive the tether and comprising the additional step of tying the tether through the at least one aperture dimensioned to receive the tether and the superior spinous process.

16. The method of claim 13, wherein a zip cable is used and further comprising the additional step of attaching the zip cable to the implant at least one of before and after insertion of the implant; wrapping the zip cable around the superior spinous process and feeding the zip cable through a base fixed to the implant on the opposite side of the spinous process.

17. The method of claim 1, wherein the implant is made of non-bone material.

18. The method of claim 17, wherein the implant is made from one of polyetheretherketone and polyetherketoneketone.

19. The method of claim 1, wherein verifying the position of the implant includes ensuring a top portion of the first marker aligns with the superior spinous process and a bottom portion of the first marker aligns with the inferior spinous process.

20. The method of claim 19, wherein verifying the position of the implant includes ensuring the second of the radio-opaque markers is positioned on one side of the inferior spinous process and the third marker is positioned on the other side of the inferior spinous process.

21. The method of claim 20, wherein the verifying the position of the implant includes ensuring the second of the radio-opaque markers is not positioned to far anteriorly and the third radio-opaque marker is not positioned too far posteriorly.

22. A method for treating spinal stenosis, comprising:
gaining access to an inter spinous process space between a superior spinous process and an inferior spinous process;
abrading a portion of only one of the superior and inferior spinous processes;
inserting an implant in the inter spinous process space, the implant having opposing lateral sides, an anterior side, and a posterior side, wherein said anterior side includes at least one pair of apertures for releasably engaging an insertion tool;
verifying the position of the implant by observing on a radiographic image the position of three radio-opaque markers embedded in the implant, a first of the radio-opaque markers being positioned at the center of the implant in a superior-inferior orientation, a second of the radio-opaque markers being positioned in one of said lateral sides and in an anterior aspect of the implant, and a third of the radio-opaque markers being positioned in the opposite lateral side and in a posterior aspect of the implant; and
coupling the implant to the abraded spinous process.

* * * * *